United States Patent
Schabbach et al.

(10) Patent No.: US 9,402,959 B2
(45) Date of Patent: Aug. 2, 2016

(54) ASSEMBLY FOR A DRUG DELIVERY DEVICE AND DRUG DELIVERY DEVICE

(75) Inventors: Michael Schabbach, Frankfurt am Main (DE); Serpil Heger, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 104 days.

(21) Appl. No.: 13/393,324

(22) PCT Filed: Sep. 21, 2010

(86) PCT No.: PCT/EP2010/063841
§ 371 (c)(1),
(2), (4) Date: Jun. 22, 2012

(87) PCT Pub. No.: WO2011/036133
PCT Pub. Date: Mar. 31, 2011

(65) Prior Publication Data
US 2012/0259285 A1 Oct. 11, 2012

(30) Foreign Application Priority Data
Sep. 23, 2009 (EP) .................................... 09171133

(51) Int. Cl.
*A61M 5/315* (2006.01)
*A61M 5/20* (2006.01)
*A61M 5/31* (2006.01)

(52) U.S. Cl.
CPC ......... *A61M 5/31525* (2013.01); *A61M 5/3146* (2013.01); *A61M 5/31533* (2013.01); *A61M 5/20* (2013.01); *A61M 5/31583* (2013.01); *A61M 2005/3125* (2013.01); *A61M 2205/584* (2013.01)

(58) Field of Classification Search
CPC ............ A61M 5/3271; A61M 5/3243; A61M 5/3137; A61M 5/31551; A61M 5/24; A61M 5/31563; A61M 5/3129; A61M 2205/583
USPC .................. 604/198, 189, 207, 209, 211; 128/200.14
See application file for complete search history.

(56) References Cited

U.S. PATENT DOCUMENTS

RE32,974 E * 7/1989 Porat et al. .................... 604/208
5,271,527 A 12/1993 Haber et al.
(Continued)

FOREIGN PATENT DOCUMENTS

WO      2007/121915      11/2007
WO      WO 2008/042701   * 4/2008

OTHER PUBLICATIONS

European Search Report for EP App. No. 09171133, completed Feb. 18, 2010.
(Continued)

*Primary Examiner* — Kami A Bosworth
*Assistant Examiner* — Matthew A Engel
(74) *Attorney, Agent, or Firm* — McDonnell Boehnen Hulbert & Berghoff LLP

(57) ABSTRACT

An assembly for a drug delivery device is provided for. The assembly may comprise a housing body having a longitudinal axis. It may have a drive assembly having a drive member, the drive member being configured to be axially displaced with respect to the housing body during operation of the drive assembly for setting and/or dispensing a dose of the drug. The assembly may have a display assembly having a display and an indicator element, the indicator element being axially displaceable with respect to the housing body along the longitudinal axis or the indicator element being rotationally displaceable with respect to the housing body around a rotational axis which is inclined, in particular perpendicular, to the longitudinal axis. The display may be configured such that it displays a first state when the indicator element is in a first position and switches to a second state when the indicator element is displaced away from the first position. The drive assembly may be configured such that the drive member transfers a force to the indicator element which force displaces the indicator element away from the first position when the drive assembly is operated for a first time. Further, a drug delivery device is provided for.

14 Claims, 4 Drawing Sheets

(56) References Cited

U.S. PATENT DOCUMENTS

| | | | | |
|---|---|---|---|---|
| 5,279,585 A * | 1/1994 | Balkwill | A61M 5/3158 | 222/309 |
| 5,279,586 A * | 1/1994 | Balkwill | A61M 5/3158 | 222/309 |
| 5,482,163 A * | 1/1996 | Hoffman | A61J 7/04 | 116/309 |
| 5,693,027 A * | 12/1997 | Hansen | A61M 5/24 | 604/200 |
| 5,728,074 A * | 3/1998 | Castellano | G06F 19/3468 | 600/309 |
| 8,001,963 B2 * | 8/2011 | Giroux | A61M 15/08 | 128/200.14 |
| 8,202,255 B2 * | 6/2012 | Saiki | A61M 5/31551 | 604/181 |
| 8,298,194 B2 * | 10/2012 | Moller | A61M 5/24 | 604/181 |
| 8,348,904 B2 * | 1/2013 | Petersen | A61M 5/24 | 604/207 |
| 2002/0022821 A1 * | 2/2002 | Eilersen | G06K 7/10 | 604/404 |
| 2002/0165500 A1 * | 11/2002 | Bechtold | A61M 5/2033 | 604/209 |
| 2003/0120222 A1 * | 6/2003 | Vaillancourt | A61M 5/321 | 604/263 |
| 2004/0024368 A1 * | 2/2004 | Broselow | A61M 5/31525 | 604/207 |
| 2008/0051692 A1 * | 2/2008 | Petersen | A61N 1/303 | 604/20 |
| 2009/0062728 A1 * | 3/2009 | Woo | A61M 5/1723 | 604/66 |
| 2009/0062730 A1 * | 3/2009 | Woo | A61M 5/1723 | 604/66 |
| 2012/0071834 A1 * | 3/2012 | Harms | A61M 5/3129 | 604/189 |
| 2012/0089098 A1 * | 4/2012 | Boyd | A61M 5/24 | 604/189 |
| 2012/0101445 A1 * | 4/2012 | Jansen | A61M 5/24 | 604/189 |
| 2012/0203184 A1 * | 8/2012 | Selz | A61M 5/3146 | 604/189 |
| 2012/0232517 A1 * | 9/2012 | Saiki | A61M 5/31551 | 604/500 |
| 2012/0253288 A1 * | 10/2012 | Dasbach | A61J 7/04 | 604/189 |
| 2012/0310172 A1 * | 12/2012 | MacDonald | A61M 5/31525 | 604/207 |
| 2012/0330228 A1 * | 12/2012 | Day | A61M 5/14244 | 604/82 |
| 2013/0072897 A1 * | 3/2013 | Day | A61M 5/1452 | 604/500 |
| 2013/0079708 A1 * | 3/2013 | Wimpenny | A61M 5/002 | 604/65 |
| 2013/0096511 A1 * | 4/2013 | MacArthur | A61J 1/06 | 604/189 |
| 2013/0131601 A1 * | 5/2013 | Pommereau | A61M 5/3129 | 604/189 |
| 2013/0226095 A1 * | 8/2013 | Dasbach | A61J 7/04 | 604/189 |

OTHER PUBLICATIONS

International Search Report for International App. No. PCT/EP2010/063841, completed Oct. 11, 2010.

* cited by examiner

ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2010/063841 filed Sep. 21, 2010, which claims priority to European Patent Application No. 09171133.3 filed on Sep. 23, 2009. The entire disclosure contents of these applications are herewith incorporated by reference into the present application.

FIELD OF INVENTION

The present disclosure relates to an assembly suitable for use in a drug delivery device by which at least one dose of a medicinal product can be administered, for example in a pen-type injector. According to one aspect, the present disclosure relates to a drug delivery device where in particular a user may operate the drug delivery device. According to a further aspect, the disclosure relates to a method for operating the drug delivery device.

BACKGROUND

During the manufacture and assembly of drug delivery devices, tolerances can occur, for example in the size of the elements of the drug delivery device and/or in the position of the elements of the drug delivery device with respect to each other. Therefore, a priming step, sometimes also denoted as a setup step or activation step, may be required before the drug delivery device can be used to administer a medication dose of the drug to a patient with the required accuracy.

An assembly for a drug delivery device should be provided which facilitates making available information about whether the priming step has already been carried out or not.

SUMMARY

According to at least one aspect, an assembly is provided for. The assembly may be an assembly for a drug delivery device.

According to at least one aspect, the assembly comprises a housing body. The housing preferably has a longitudinal axis. The housing body preferably has a proximal end and a distal end. The longitudinal axis may preferably extend between the proximal end and the distal end.

According to at least one aspect, the assembly comprises a drive assembly. Preferably, the drive assembly is operable for setting and/or dispensing a dose of a drug. The drive assembly may comprise a drive member. The drive member is preferably configured to be axially displaced with respect to the housing body, in particular along the longitudinal axis, during operation of the drive assembly for setting and/or dispensing a dose of the drug.

According to at least one aspect, the assembly comprises a display assembly. The display assembly preferably has a display. The display may be operable to display a first state and a second state, which second state is in particular different from the first state.

Preferably, the display assembly further comprises an indicator element. In one embodiment, the indicator element is axially displaceable with respect to the housing body. In particular, the indicator element is axially displaceable with respect to the housing body along the longitudinal axis.

Alternatively or additionally, the indicator element may be rotationally displaceable with respect to the housing body around a rotational axis. In one embodiment, the rotational axis is inclined to the longitudinal axis. The inclined rotational and longitudinal axes may be skew, i.e. they are not parallel and do not intersect. Alternatively, the rotational axis and the longitudinal axis may intersect. In particular, the inclined rotational and longitudinal axes may run perpendicular with respect to each other.

In one embodiment, the indicator element is axially displaceable and rotationally locked with respect to the housing. In another embodiment, the indicator element is rotationally displaceable and axially locked with respect to the housing.

In at least one embodiment, the housing body comprises a guide. The guide may be configured to guide the movement of the indicator axially or rotationally. The guide may be configured for retaining the indicator element in an axially or rotationally displaceable fashion.

In one embodiment, the guide may be a linear guide, sometimes also denoted as an axial guide. The linear guide may in particular be operable to retain the indicator element in an axially displaceable fashion, preferably axially displaceable along the longitudinal axis.

In another embodiment, the guide may be a hinge. The hinge may in particular be operable to retain the indicator element in a rotationally displaceable fashion and, preferably, in an axially locked fashion. For example, the indicator element is pivot-mounted by means of the hinge such that it is rotatable around the rotational axis.

According to at least one aspect, the display is configured such that it displays the first state when the indicator element is in a first position. The display preferably switches to a second state when the indicator element is displaced away from the first position. The first position may be a first axial position or a first angular position, for example.

According to at least one aspect, the drive assembly is configured such that the drive member transfers a force to the indicator element. This force may displace the indicator element away from the first position, preferably when the drive assembly is operated for a first time.

For example, the drive assembly is operated for said first time for carrying out a priming step, sometimes also denoted as a setup step or as an activation step. In this case, the first state of the display in particular indicates an un-primed configuration of the assembly and the second state of the display indicates a primed configuration of the assembly.

The priming step is, for example, provided for moving at least some constituent parts of the assembly to a predetermined position with respect to each other, such that, in particular, a subsequent dose(s) can be accurately dispensed. The assembly may be operable to set and dispense a dose with higher accuracy after the priming step than before the priming step.

According to at least one aspect, the drive assembly is configured such that the indicator element remains displaced away from the first position when the drive assembly is subsequently operated for a second time. For example, the drive assembly is operated for said second time for dispensing a dose of the drug.

According to at least one aspect, the display comprises a window. The window may be a window in the housing body. For example, the indicator element is visible through the window to display the first state. In particular, the indicator element is positioned such that it overlaps with the window in top view onto the window to display the first state.

According to at least one aspect, the indicator element is positioned such that it cannot be seen through the window when the window displays the second state. In particular, the indicator element and the window do not overlap in top view onto the window when the display displays the second state. Rather, the indicator element is preferably axially or rotationally displaced away from the window when the window displays the second state. According to at least one aspect, the drive member and/or an other—stationary or movable—element of the drive assembly is visible through the window to display the second state.

For example, the first state corresponds to a first color displayed by the display and the second state corresponds to a second color displayed by the window. The first color is expediently different from the second color. The first color may be a color of a surface of the indicator element. The second color may be a color of a surface of the drive member and/or the other element of the drive assembly.

Additionally or alternatively, the first state comprises a first symbol, e.g. a character, a numeral, a pictogram, or the like, which first symbol is displayed by the display when it is in the first state. In some embodiments, the display may display a second symbol when it displays the second state.

According to at least one aspect, the display is an electronic display, for example an LCD, an OLED-display, or an LED-display. Displays which represent another type of electrically powered light signal are also conceivable. The indicator element may be configured to act as an electrical switch in some embodiments. For example the first position corresponds to a closed electrical circuit and displacing away the indicator element from the first position opens the circuit or vice versa. In some embodiments, the display assembly comprises a control unit, for example an IC-component such as a micro controller, which control unit is configured for switching the display from displaying the first state to displaying the second state when the indicator element is displaced away from the first position.

According to at least one aspect, the drive member comprises a piston rod or consists of a piston rod. The indicator element is, for example, fixed to the piston rod or formed integrally with the piston rod. The piston rod, for example, extends along the longitudinal axis. The piston rod is, in particular, axially displaceable with respect to the housing body. A portion of the piston rod which is free of the indicator element may be visible through the window of the display assembly to display the second state.

According to at least one aspect, the assembly is configured such that the indicator element is displaced from the first position to a predetermined second position when the drive assembly is operated for said first time. The indicator element, for example, remains or is retained in the second position when the drive assembly is subsequently operated for said second time. The second position may be a second axial position or a second angular position, for example.

According to at least one aspect, the drive member and the indicator element are decoupled from each other when the indicator element is in the predetermined second position. The drive member is in particular movable independently from the indicator element when the drive member and the indicator element are decoupled from each other. For example, the drive member is inoperable to transfer a force for displacing the indicator element to the indicator element when the drive member and the indicator element are decoupled from each other.

According to at least one aspect, the drive member is configured to be displaced in a first axial direction and, subsequently, in a second axial direction when the drive assembly is operated. The second axial direction is in particular opposite to the first axial direction. For example, the first axial direction is directed from the distal end to the proximal end and the second axial direction is directed from the proximal end to the distal end.

According to at least one aspect, the drive assembly comprises a piston rod which is axially displaceable, in particular along the longitudinal axis, with respect to the drive member and to the housing body. The drive member is preferably operable to transfer a force to the piston rod for axially displacing the piston rod when the drive member is displaced in the first axial direction and/or in the second axial direction. The drive member, for example, is a drive sleeve which is arranged between the housing body and the piston rod, at least in places. The drive member, for example, is configured for carrying the piston rod with it in the second axial direction when it is displaced in the second axial direction.

According to at least one aspect, the assembly is configured such that the indicator element and the drive member are axially or rotationally displaceable with respect to each other when the drive member is moved in the first axial direction. For example, the drive member is movable independently from the indicator element in the first axial direction.

According to at least one aspect, the drive member is operable to transfer the force for displacing the indicator element away from the first position to the indicator element when the drive member is moved in the second axial direction during operation of the drive assembly for said first time. The drive member may be inoperable to transfer a force for axially or rotationally displacing the indicator element to the indicator element when the drive member is moved in the second axial direction during operation of the drive assembly for the subsequent, second time.

According to at least one aspect, the assembly is operable to hold the indicator element in a resiliently biased position before the assembly is operated for said first time. For example, the drive member is operable to hold the indicator element in the resiliently biased position. The indicator element may be resiliently biased in a radial direction, when it is in the resiliently biased position. The radial direction is in particular a direction perpendicular to the axial direction defined by the longitudinal axis. The indicator element is, for example, at least partially arranged between the drive member and the housing body, when it is in the resiliently biased position.

According to at least one aspect, the drive member is inoperable to transfer the force for displacing the indicator element away from the first position to the indicator element when the indicator element is in the resiliently biased position and is operable to transfer said force to the indicator element when the latter is in an interaction position, which is different from the resiliently biased position. For example, the resiliently biased position and the interaction position correspond to a first radial position and to a second radial position of the indicator element, respectively.

According to at least one aspect, the drive member is in a rest position before the drive assembly is operated for the first time. Preferably, the drive member is operable to hold the indicator element in the resiliently biased position when the drive member is in the rest position. The assembly may be configured such that the indicator element can move radially or rotationally from the resiliently biased position to the interaction position when the drive member is moved by a predetermined distance from the rest position in the first axial direction, for example to a dose-set position. The dose-set position may be the position of the drive member which is closest to the proximal end of the housing body.

The resilient bias in particular effects a spring force. The indicator element is in particular moved from the resiliently biased position to the interaction position by means of the spring force. In particular, the indicator element snaps from the resiliently biased position to the interaction position when the drive member is displaced from the rest position to the dose set position during operation of the drive assembly for said first time. The indicator element may be fully or partly relaxed when in interaction position.

According to at least one aspect, the indicator element has an elastically deflectable end. For example, the elastically deflectable end of the indicator element is in a deflected position when the indicator element is in the resiliently biased position. The elastically deflectable end may, for example, be arranged between the drive member and the housing when it is in the deflected position.

The elastically deflectable end of the indicator element is preferably in an undeflected position when the indicator element is in the interaction position. For example, the elastically deflectable end snaps from the deflected to the undeflected position when the drive member is displaced in the first axial direction from the rest position to the dose-set position during operation of the drive assembly for the first time.

According to one aspect, the assembly is configured such that an end, in particular a distal end, of the drive member may be pressed against or abut the indicator element, in particular the deflectable end of the indicator element, for displacing the indicator element away from the first position when the indicator element is in the interaction position. For example, the drive member and the indicator element overlap in top view along the axial direction when the indicator element is in the interaction position. In one embodiment, the assembly is configured such that an end face of the drive member may be pressed against the indicator element, in particular for axially displacing the indicator element. In another embodiment, the drive member comprises a catch, which may be designed as a pocket or as a protrusion, for example, and the catch may be pressed against the indicator element for axially or rotationally displacing the indicator element. The catch is preferably operable to engage with the indicator element when the latter is in the interaction position.

According to at least one aspect, a drug delivery device is provided for. The drug delivery device comprises an assembly as described above. The drug delivery device is preferably configured for dispensing at least one dose of the drug. The drug delivery device may be configured for dispensing a plurality of doses of the drug. The dose or the doses may be fixed doses. Fixed doses in particular comprise a predetermined amount of the drug. If the drug delivery device is configured for dispensing a plurality of fixed doses, each of the fixed doses has the same amount of drug. The amount is expediently not individually adjustable by the user.

According to at least one aspect, the drug delivery device comprises a cartridge, sometimes also denoted as a container, which is configured for retaining the dose or the plurality of doses of the drug. The drive assembly is in particular configured for dispensing the drug from the cartridge.

According to at least one further aspect, a method for operating the drug delivery device is provided for.

According to one method step, the drug delivery device is provided with the display displaying the first state. For example, the drug delivery device is in an unprimed configuration during this method step. The drug delivery device may be provided with the drive member in the rest position and the indicator element in the resiliently biased position. For example, the drug delivery device may be provided with the elastically deflectable end of the indicator element being arranged in the deflected position, in particular between the drive sleeve and the housing.

According to a subsequent method step, the display is switched to displaying the second state by operating the drive assembly for a first time, in particular by operating the drive assembly for carrying out the priming step. A small amount of drug, e.g. an amount less than the amount in a fixed dose, may be dispensed during this method step. The drug may be dispensed into the air during this method step.

According to at least one aspect, the drive member is axially moved by a predetermined distance from the rest position in the first axial direction, e.g. to the dose-set position, during operation of the drive assembly for the first time. Subsequently, the indicator element may be moved from the resiliently biased position to the interaction position by the spring force induced by the resilient bias. For example, the deflectable end of the strip snaps into the undeflected position.

According to at least one aspect, the drive member is subsequently moved in the second axial direction. Preferably, the drive member, in particular the drive sleeve, also carries the piston rod with it in the second axial direction. Preferably, the drive member is returned to the rest position by the displacement in the second axial direction.

In one embodiment, the drive member carries the indicator member with it in the second axial direction, away from the first position. The drive member may carry the indicator element with it to the predetermined second position. In another embodiment, the movement of the drive member in the second axial direction is converted into a rotational movement of the indicator element around the rotational axis, such that the indicator element is displaced away from the first position, preferably to a predetermined second position.

According to at least one aspect, the method may have an additional, subsequent method step, wherein a dose of the drug is dispensed by actuating the drive assembly for a second time. The dose of the drug may be dispensed for administering the drug to a patient or for testing purposes, for example. During this method step, the display is, in particular, retained in the second state. The display may be in the second state, preferably the display is permanently kept in the second state, when regular, i.e. non-priming, doses are dispensed.

According to at least one aspect—when the drive assembly is operated for the second time—the drive member is moved from the rest position in the first axial direction to the dose-set position and then in the second axial direction to the rest position, again, and it carries the piston rod with it in the second axial direction. However, the indicator element preferably remains in the predetermined second position when the drive member is displaced in the first and second axial direction during operation of the drive assembly for the second time.

The term "drug delivery device" shall preferably mean a single-dose or multi-dose or pre-set dose or pre-defined, disposable or re-useable device designed to dispense a user selectable or pre-defined dose, i.e. fixed dose, of a medicinal product, preferably multiple pre-defined doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or an electronic mechanism. Additionally, said device may contain components designed to monitor physiological properties such as blood glucose levels, etc. Furthermore, the device may comprise a needle or may be needle-free. In particular, the term "drug delivery device" preferably means a disposable needle-based pen-type device providing multiple pre-defined doses having mechanical and manual dose delivery and dose selection mechanisms, which is designed for use by persons without formal medical training such as patients. Preferably, the drug delivery device is of the injector-type.

The term "housing body" shall preferably mean any exterior housing ("main housing", "body", "shell") or interior housing ("insert", "inner body") having a unidirectional axial coupling to prevent proximal movement of specific components. The housing may be designed to enable the safe, correct, and comfortable handling of the assembly, the drug delivery device or any of its mechanism(s). Usually, it is designed to house, fix, protect, guide, and/or engage with any of the inner components of the drug delivery device (e.g., the drive assembly, cartridge, plunger, piston rod), for example by limiting the exposure to contaminants, such as liquid, dust, dirt etc. In general, the housing body may be unitary or a multipart component of tubular or non-tubular shape. Usually, the exterior housing serves to house a cartridge from which a number of doses of a medicinal product may by dispensed. Preferably, the exterior housing is provided with a plurality of maximum dose stops adapted to be abutted by an axial stop provided on the drive member.

The term "drive member" shall preferably mean any component adapted to operate through/within the housing body, designed to translate axial movement through/within the assembly or the drug delivery device, respectively, e.g. from an actuation component such as a push button to the piston rod. In a preferred embodiment the drive member is further releasably engaged with the piston rod. The term "releasably engaged" shall preferably mean that two components of instant mechanism or device are joined for translation of force or movement in one direction only, preferably during dispense. The drive member may be of unitary or multipart construction.

The term "piston rod" shall preferably mean a component adapted to operate through/within the housing body, designed to translate axial movement through/within the assembly or the drug delivery device, respectively, preferably from the drive member to the piston, e.g. for the purpose of discharging/dispensing an injectable product. Said piston rod may be flexible or not. It may be a simple rod, a lead-screw, a rack and pinion system, a worm gear system, or the like. The term "piston rod" shall further preferably mean a component having a circular or non-circular cross-section. It may be made of any suitable material known by a person skilled in the art and may be of unitary or multipart construction. In a preferred embodiment, the piston rod comprises a series of one or more sets of longitudinally spaced ribs and/or indentations.

The "distal end" of the assembly, the device or a component of the device, e.g. of the housing body, shall preferably mean the end, which is to be disposed closest or which is disposed closest to the dispensing end of the device. The "proximal end" of the assembly, the device or a component of the device, e.g. the housing body, shall mean the end, which is to be disposed furthest away or which is furthest away from the dispensing end of the device.

The terms "drug", "medicinal product", "medication" or "medicament", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Without any limitation, e.g. to the scope of the claims, preferred embodiments are described below with reference to the drawings in which:

Figure 1A:
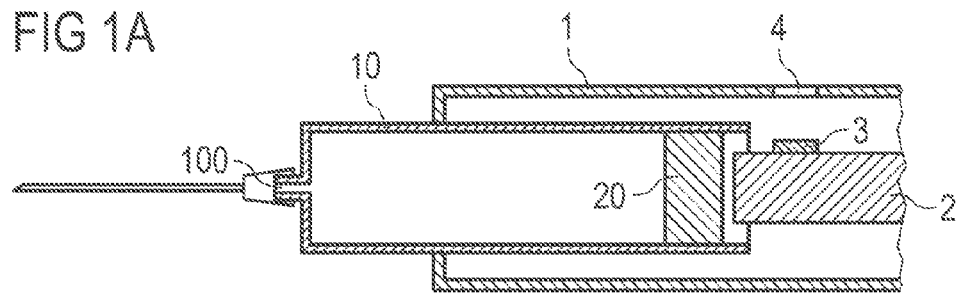
FIG. 1A shows a schematic sectional view of an assembly for a drug delivery device according to a first exemplary embodiment in first, e.g. unprimed, configuration.

Like elements, elements of the same kind, and similarly acting elements are provided with the same reference numerals in the figures. The figures and the size relations of the elements in the figures are not to be regarded as being true to scale. Rather, single elements can be exaggerated in size for a better representation and/or comprehension.

DETAILED DESCRIPTION

Figure 2A:
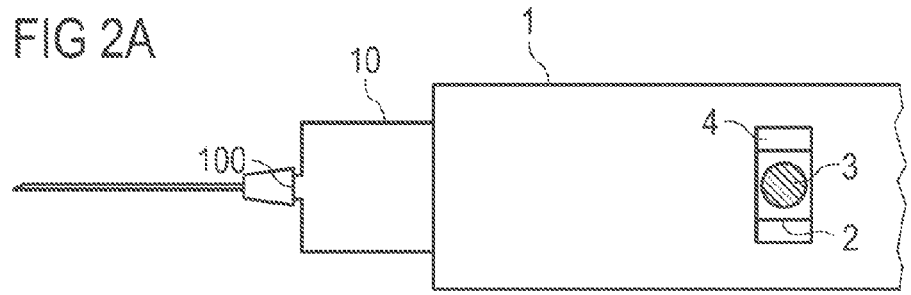
FIG. 2A shows a schematic side view of the assembly of FIG. 1A.

FIG. 1A shows a schematic cross-sectional view of an assembly for a drug delivery device in a first configuration, e.g. an unprimed configuration. FIG. 2A shows a schematic side view of the assembly of FIG. 1A.

The assembly is suitable for use with a drug delivery device. The drug delivery device may additionally comprise a cartridge 10 which is designed for retaining at least one dose of a drug, in particular a liquid medicament. The cartridge 10 has an opening 100 defining a dispensing end of the device. Remote from the dispensing end, the cartridge 10 may have a piston 20. The piston is movably retained within the cartridge.

The assembly comprises a housing body 1. The housing body has a distal end which is closest to the dispensing end of the cartridge 10 and a proximal end opposite of the distal end.

The assembly further comprises a drive assembly having a drive member, the drive member being embodied in form of a piston rod 2 in the first exemplary embodiment. In the present embodiment, piston rod 2 is operable to axially displace piston 20 towards the dispensing end.

The piston rod 2 is axially displaceable with respect to the housing body 1. The drive assembly may comprise at least one additional element (not explicitly shown in FIGS. 1A, 1B, 2A, and 2B) for transferring a force to the piston rod for axially displacing the piston rod 2 during operation of the drive assembly.

The assembly further comprises a display assembly having an indicator element 3 and a window 4. The window 4 is comprised by the housing body 1.

Indicator element 3 is fixed on the piston rod 2. Indicator element 3 can, for example, be an adhesive label which is bonded to the piston rod. In another variant, indicator element 3 can be a paint mark, which is applied to the piston rod, for example by printing.

The indicator element, for example, has a first color, at least at its surface facing the window 4. The piston rod 2, preferably, has a second color which is expediently different from the first color. For example, the first color may be red and the second color may be green. Red may indicate that there is need for priming and green may indicate that the device has already been primed.

In the first configuration, as shown in FIGS. 1A and 2A, indicator element 3 is in a first position which is a first axial position in the present embodiment. In this configuration, indicator element 3 is positioned such that it is visible through window 4 from the exterior of the housing body 1. In particular, indicator element 3 laterally overlaps with window 4 in top view of window 4.

Figure 1B:
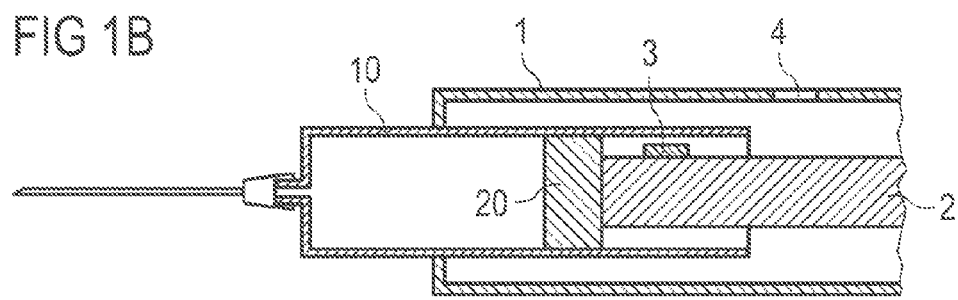
FIG. 1B shows a schematic sectional view of the assembly according to the first exemplary embodiment in a second, e.g. primed, configuration.
Figure 2B:
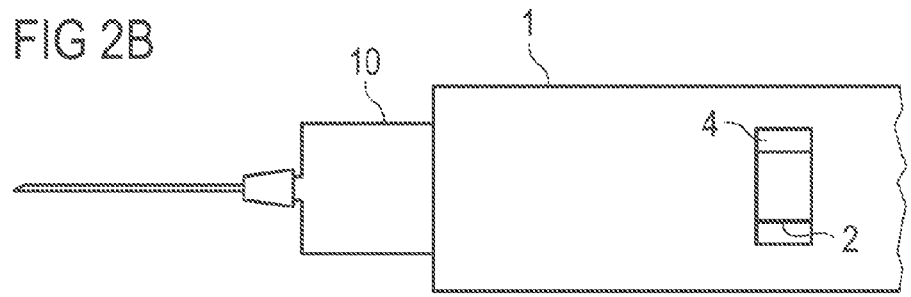
FIG. 2B shows a schematic side view of the assembly of FIG. 1B.

FIG. 1B shows a schematic cross-sectional view of the assembly according to the first exemplary embodiment in a second, e.g. primed, configuration. FIG. 2B shows a schematic side view of the assembly according to the first exemplary embodiment in the second configuration.

In the second configuration, the drive assembly has been operated at least for a first time. Since the piston rod 2 is displaced axially in the direction of the distal end when the drive assembly is operated, a distal end of the piston rod 2 is positioned closer to the distal end of the housing body 1 in the second configuration than in the first configuration.

Indicator element 3, which is fixed on the piston rod 2, therefore is displaced away from the first axial position, as well. In particular, it is positioned such that it is not visible through the window 4 from the exterior of the housing body 1 anymore. In other words, the indicator element 3 and the window 4 do not overlap in top view of the window 4.

The display displays a first state when the indicator element 3 is in the first axial position. When the indicator element 3 is displaced away from the first position, so that it is, in particular, not visible through window 4, the display displays a second state.

For example, the first and second state are distinguishable by their color. For example, the first state corresponds to the first color, i.e. the color of the indicator element 3, and the second state corresponds to the second color, i.e. the color of the piston rod 2.

When the drive assembly is subsequently operated for a second time, for example for dispensing a dose of the drug, the piston rod 2 is displaced further towards the distal end of the housing body 1. It carries the indicator element 3 with it, so that the latter does not return to the first axial position. Therefore, also the display does not return to the first state but keeps indicating the second state.

The first configuration can, for example, be an unprimed configuration. Tolerances, which can be present, for example, due to manufacturing or assembling of the assembly and/or the drug delivery device, may lead to an uncertainty in the relative positions of the constituent parts of the assembly and/or the drug delivery device. For example, the piston rod 2 can be axially spaced from the piston 20 in the unprimed configuration.

Such tolerances may lead to an insufficient dose accuracy. For example, before drug may be dispensed with high accuracy, the gap between piston and piston rod has to be overcome. This gap may, of course, differ in different devices due to differing tolerances during production. Thus, if the piston rod, as it is usual in fixed dose devices, is displaced by a predetermining fixed distance during each dispensing operation, the first dose would be inaccurate and, in particular, different from subsequent doses, because no drug is expelled while overcoming the gap. Therefore, a priming step, also known as setup step, may be performed by operating the drive assembly for the first time. The constituent parts of the assembly and, as the case may be, of the drug delivery device are brought into well defined, in particular in predetermined positions with respect to each other when the drive assembly is operated for carrying out the priming step. In this way, the dispensed amount of drug can be determined with sufficient accuracy when the drive assembly is operated subsequently for a second time or a plurality of second times.

The drive assembly may be configured to extract a certain amount of drug, the so-called priming dose, out of the cartridge of the drug delivery device when it is operated for the first time in order to carry out the priming step. The amount of drug in the prime dose can be smaller than the amount of drug in the medication doses which are to be dispensed when the drive assembly is operated for the subsequent second time(s).

Figure 3A:
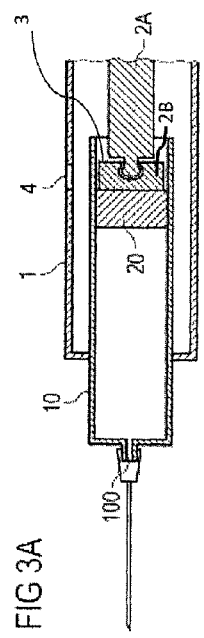
FIG. 3A shows a schematic cross-sectional view of an assembly for a drug delivery device according to a second exemplary embodiment in first, e.g. unprimed, configuration.
Figure 3B:
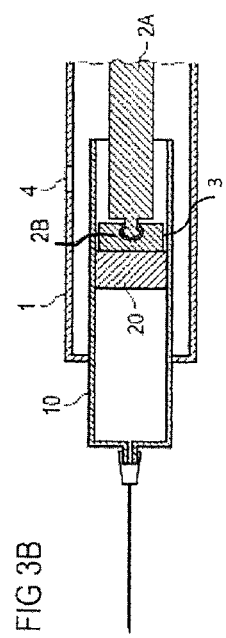
FIG. 3B shows a schematic cross-sectional view of the assembly according to the second exemplary embodiment in a second, e.g. primed, configuration.
Figure 4A:
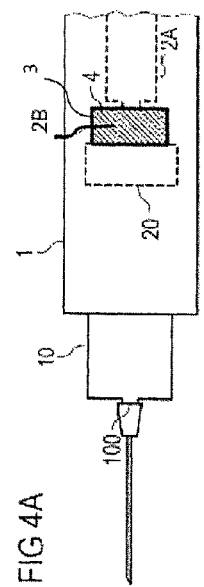
FIG. 4A shows a schematic side view of the assembly of FIG. 3A.
Figure 4B:
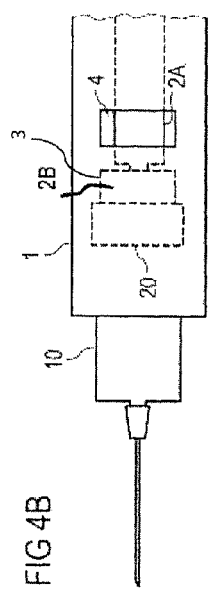
FIG. 4B shows a schematic side view of the assembly of FIG. 3B.

FIG. 3A shows a schematic cross-sectional view of an assembly for a drug delivery device according to a second exemplary embodiment in a first configuration. FIG. 4A shows a schematic side view of the assembly according to the second exemplary embodiment in the first configuration. FIG. 3B shows a schematic cross-sectional view of the assembly according to the second exemplary embodiment in a second configuration. FIG. 4B shows the assembly according to FIG. 3B in a schematic side view.

The assembly according to the second exemplary embodiment is different from the assembly according to the first embodiment in that the indicator element 3 is not bonded to a sidewall of the piston rod 2. Rather, indicator element 3 is formed integrally with a section of piston rod 2 in the second exemplary embodiment.

More specifically, the piston rod 2 comprises a lead screw 2A and a bearing 2B in the present embodiment. Lead screw 2A is rotatable but not axially displaceable with respect to the bearing 2B. Lead screw 2A may have an external or internal thread (not shown in the figures) for engaging with the housing body 1 and/or for engaging with a further element of the drive assembly which further element may be provided for axially displacing the piston rod 2.

The indicator element 3 is formed integrally with the bearing 2B in the present embodiment. For example, the bearing 2B—or at least a surface of the bearing 2B—has a first color and the lead screw 2A—or at least a surface of the lead screw 2A—has a second color which is different from the first one. Similarly to the first exemplary embodiment, the bearing 2B can be provided with a mark, for example a symbol, or a mark can be engraved into the bearing in a variant of this embodiment.

In the first configuration, the bearing 2B is visible through window 4. In a drug delivery device with a cartridge 10, the cartridge 10 has preferably a transparent or translucent material. In this way, the indicator element 3 can be seen through the cartridge 10 when the cartridge is arranged between the indicator element 3 and the window 4.

When the indicator element 3 is in the first axial position, such that it is visible through the window 4, the display displays a first state, corresponding, for example, to the first color, i.e. the color of the bearing 2B. The first state may, for example, indicate an unprimed configuration.

In the second configuration, shown in FIGS. 3B and 4B, the drive assembly has been operated for the first time. The piston rod 2A, 2B has been displaced towards the distal end of the housing body 1 so that indicator element 3, which is formed integrally with the piston rod 2A, 2B, is displaced away from the first axial position.

In particular, bearing 2B is displaced away from window 4, so that it is no longer visible through the window 4. Instead, for example, lead screw 2A is visible through the window 4 in the second configuration. In this way, the display displays a second state, corresponding to the second color, i.e. the color of the lead screw 2A.

FIGS. 5A, 5B, 5C, and 5D show schematic side views of an assembly for a drug delivery device according to a third exemplary embodiment. In the side views of FIGS. 5A-5D, a section of the housing 1 has been cut away to allow viewing the drive assembly and the display assembly.

Figure 5A:
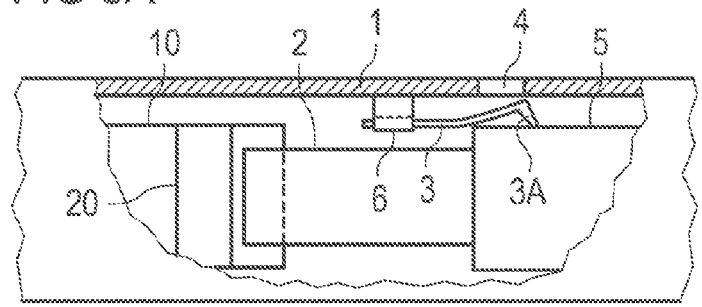
FIG. 5A shows a schematic side view with the housing body cut open of an assembly for a drug delivery device according to a third exemplary embodiment in a first, e.g. unprimed, configuration.
Figure 5B:
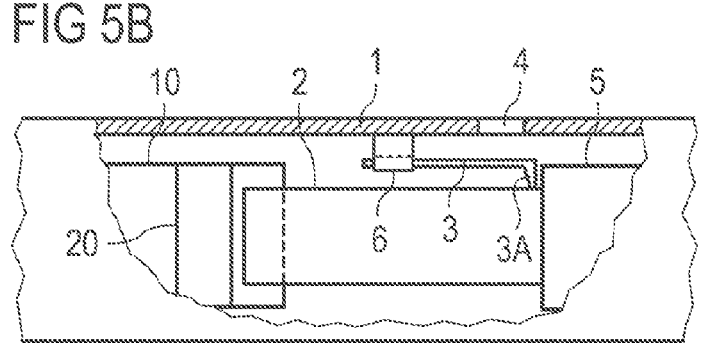
FIG. 5B shows a schematic side view with the housing cut open of the assembly according to the third exemplary embodiment in a second configuration, e.g. a dose set configuration, during the operation of the drive assembly for the first time.
Figure 5C:
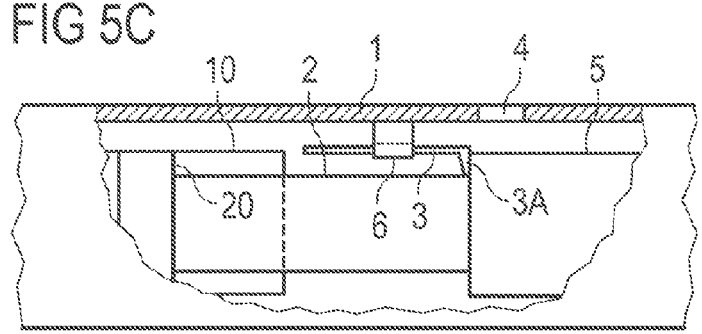
FIG. 5C shows a schematic side view of the assembly according to the third exemplary embodiment in a third configuration, e.g. a primed configuration.
Figure 5D:
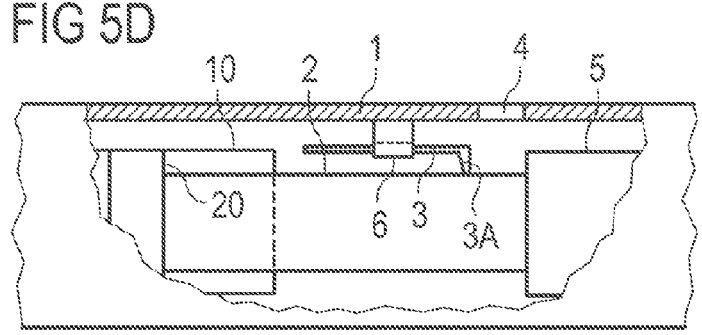
FIG. 5D shows a schematic side view with the housing body cut open of the assembly according to the third exemplary embodiment in a fourth configuration, e.g. a dose set configuration during operation of the drive assembly for the second time.

FIG. 5A shows the assembly in a first configuration, e.g. an unprimed configuration. FIG. 5B shows the assembly in a second configuration, e.g. a dose set configuration for setting the prime dose. FIG. 5C shows the assembly in a third configuration, e.g. a prime dose dispensed position. FIG. 5D shows the assembly in a fourth configuration, e.g. a dose set configuration for setting a medication dose.

The assembly according to the third exemplary embodiment is different from the first and second embodiment in that the indicator element 3 is not integrated with the piston rod 2 or fixed on the piston rod 2. Rather, the indicator element 3 of the third exemplary embodiment is a strip which is retained in a guide, which is a linear guide 6 in the present embodiment. The linear guide 6 is fixed to the housing body or formed integrally with the housing body 1. The strip 3 is visible through the window 4 of the housing body 1 when it is in the first position which is a first axial position in this embodiment.

According to the third exemplary embodiment, the drive assembly has a drive sleeve 5 which is axially displaceable in a first axial direction from a rest position to a dose set position. The dose set position is in particular the position of the drive sleeve 5 which is closest to the proximal end of the housing body 1. Further, the drive sleeve 5 is axially displaceable in a second axial direction from the dose set position to the rest position. The rest position, in particular, is the axial position of the drive sleeve 5 which is closest to the distal end of the housing body 1.

The drive assembly is preferably configured such that the drive sleeve 5 carries the piston rod 2 with it in the second axial direction when it is moved from the dose set position to the rest position. The drive assembly may be designed such that the drive sleeve 5 does not displace the piston rod 2 in an axial direction when it moves in the first axial direction from the rest position to the dose set position.

The strip 3 has an elastically deflectable end 3A. For example, the proximal end of the strip is the elastically deflectable end 3A.

The assembly is configured such that the drive sleeve 5 holds the strip 3 in a resiliently biased position when the strip 3 is in the first axial position and the drive sleeve 5 is in the rest position (see FIG. 5A). In the resiliently biased position the elastically deflectable end 3A is radially outwardly deflected. For example, the deflectable end 3A of the strip 3 has a radially inwardly directed nose or fin which bears on a surface of the drive sleeve 5 to increase the amount of deflection.

Starting from this configuration, when the drive sleeve 5 is axially displaced in the first axial direction to the dose set position during the operation of the drive assembly for the first time, drive sleeve 5 and the strip 3 are axially displaced with respect to each other. For example, drive sleeve 5 moves independently from strip 3 in the first axial direction so that strip 3 is not axially displaced when the drive sleeve 5 is moved from the rest position to the dose set position.

Expediently, the assembly is configured such that the distal end of the drive sleeve 5 is closer to the proximal end of the housing body 1 than the proximal end of strip 3—which preferably is the elastically deflectable end 3A—when the drive sleeve is in the dose-set position. In this way, the deflectable end 3A can move radially inwardly from the deflected position to an undeflected position. In particular, the spring force induced by the resilient bias moves the deflectable end 3A from the resiliently biased position radially inwardly towards an interaction position once the drive sleeve 5 has reached the dose-set position during the first operation of the drive assembly (see FIG. 5B).

In the interaction position, the drive sleeve 5 is operable to transfer the force for displacing the strip 3 away from the first axial position. In the resiliently biased position, drive sleeve 5 is in particular inoperable to axially move the strip 3.

For example, the strip 3, in particular at least the nose or fin of the deflectable end 3A of the strip 3, overlaps with the drive sleeve 5 in top view along the axial direction such that the distal end of the drive sleeve 5 can be pressed against the deflectable end 3A of the strip.

When the drive sleeve 5 is moved in the second axial direction from the dose-set position back to the rest position, it carries the strip 3 with it and displaces it away from the first axial position to a predetermined second position, which is a predetermined second axial position in the present embodiment.

In the second axial position, the strip 3 is no longer visible through the window 4 from the outside of the hollow housing body 1. In other words, it does not overlap with the window 4 in top view onto the window 4 (see FIG. 5C). Rather, drive sleeve 5 is visible through the window and laterally overlaps with the window 4 in top view of window 4 when it is in the rest position. Drive sleeve and indicator element (strip 3) may be coded with different colors.

When the drive assembly is operated for a second time, drive sleeve 5 is moved in the first axial direction again. Strip 3 remains in the predetermined second axial position when drive sleeve 5 is moved in the first axial direction to the dose-set position, during operation of the drive assembly for the second time (see FIG. 5D). In this fourth configuration, piston rod 2 is visible through the window 4. Piston rod and indicator element (strip 3) may be coded with different colors.

Subsequently, in particular for dispensing a medication dose of the drug, drive sleeve 5 is returned from the dose set position to the rest position by a movement in the second axial direction. Also during this displacement in the second axial direction of drive sleeve 5, strip 3 remains in the predetermined second position, whereas the piston rod 2 is displaced in the second axial direction by the drive sleeve 5.

The drive assembly comprising window 4 and indicator element 3 in this embodiment is, for example, configured for displaying a first state corresponding to a first color. The first color is in particular the color of the strip 3 or at least of a surface of the strip 3 which surface is proximate to the window 4. In addition, the display assembly is configured for displaying a second state, corresponding to a second color. The second color is in particular the color of the drive sleeve 5 and/or of the piston rod 2 or of respective surfaces of the drive sleeve 5 and the piston rod 2.

Figure 6A:
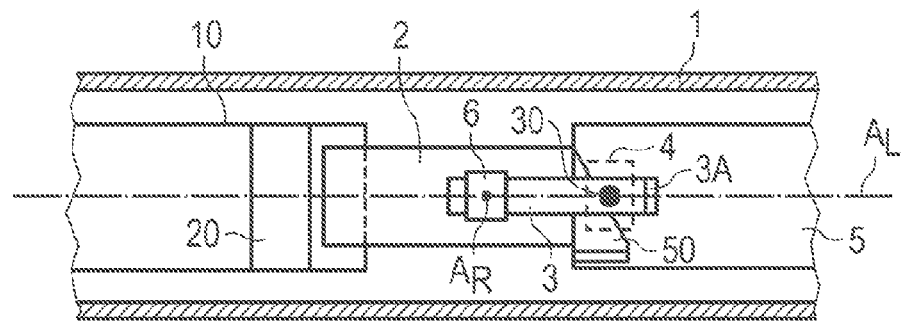
FIG. 6A shows a schematic side view of an assembly for a drug delivery device with the housing body partially cut away according to a fourth exemplary embodiment in a first, e.g. unprimed, configuration.
Figure 6B:
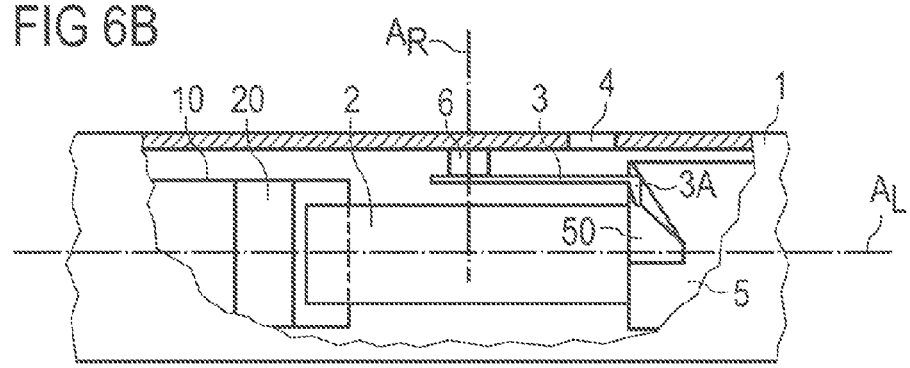
FIG. 6B shows a schematic side view with the housing body cut open of an assembly for a drug delivery device according to the fourth exemplary embodiment in a second configuration, e.g. a dose set configuration, during the operation of the drive assembly for the first time.
Figure 6C:
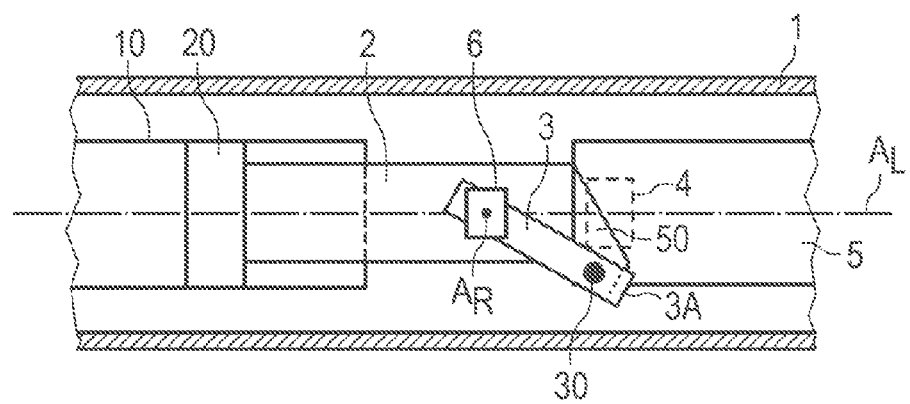
FIG. 6C shows a schematic side view of the assembly for a drug delivery device according to the fourth exemplary embodiment with the housing body partially cut away in a third, e.g. primed, configuration.

FIGS. 6A, 6B, and 6C show respective schematic side views of an assembly for a drug delivery device according to a fourth exemplary embodiment. In order to permit the drive assembly and the display assembly to be viewed, the top part of the housing body 1 has been cut away in the side views of FIGS. 6A and 6C, and a section of the housing body 1 has been cut away in FIG. 6B. FIGS. 6A and 6C show the assembly from the same viewing direction. In FIG. 6B, the assembly is rotated by 90° around a longitudinal axis AL of the housing body 1 compared to FIGS. 6A and 6C.

As in the previous embodiments, the assembly comprises a cartridge 10, a piston 20, a piston rod 2, a drive sleeve 5, an indicator element 3 and a window 4. The window 4 is comprised by the housing body 1. Since the window 4 is comprised by that part of the housing body 1 which is cut away in FIGS. 6A and 6C, window 4 is only indicated with dashed lines in those figures.

Similarly to the third exemplary embodiment, the indicator element 3 is a strip which is retained in a guide 6 which is fixed to the housing body 1 or formed integrally with the housing body 1. The strip may optionally be provided with a symbol 30 such as a dot, a pictogram, a letter or a number.

In the present embodiment, the guide 6 is not a linear guide, allowing axial movement of the strip 3 along the longitudinal axis AL of the housing body 1, like in the third embodiment. Rather, the guide is a hinge 6. By means of the hinge 6, the indicator element 3 is locked with respect to axial movement along the longitudinal axis AL of the housing body 1, but it is rotatable around a rotational axis AR which is inclined with respect to the longitudinal axis AL. In the present embodiment, the longitudinal axis AL and the rotational axis AR are perpendicular to each other and intersect.

FIG. 6A shows the assembly in a first configuration, e.g. an unprimed configuration. FIG. 6B shows the assembly in a second configuration, e.g. a dose set configuration when the prime dose was set. FIG. 6C shows the assembly in a third configuration, e.g. a prime dose dispensed position.

In the first configuration (see FIG. 6A), the strip 3 is in a first position which is a first angular position with respect to the rotational axis AR in the present embodiment. For example, a main direction of extension of the strip may run parallel to the longitudinal axis AL of the housing body 1 when the strip 3 is in the first angular position. The strip 3 and in particular the symbol 30 are visible through the window 4 of the housing body 1 when the strip 3 is in the first position.

Similarly to the third embodiment, the strip 3 may have an elastically deflectable end 3A in the present embodiment. The elastically deflectable end 3A is in particular the end of the strip 3 which is remote from the hinge 6.

The assembly is configured such that the drive sleeve 5 holds the strip 3 in a resiliently biased position when the strip 3 is in the first angular position and the drive sleeve 5 is in the rest position. In the resiliently biased position the elastically deflectable end 3A is radially outwardly deflected. As in the third embodiment, the deflectable end 3A of the strip 3 may have a radially inwardly directed nose or fin which bears on a surface of the drive sleeve 5 to increase the amount of deflection.

Starting from this first configuration, when the drive sleeve 5 is axially displaced in the first axial direction to the dose set position during the operation of the drive assembly for the first time, drive sleeve 5 and the strip 3 are axially displaced with respect to each other. For example, drive sleeve 5 moves independently from strip 3 in the first axial direction. In particular, the strip 3 expediently is neither axially nor rotationally displaced when the drive sleeve 5 is moved from the rest position to the dose set position.

In contrast to the third embodiment, the distal end of the drive sleeve 5 is not closer to the proximal end of the housing body 1 than the proximal end of strip 3 when the drive sleeve is in the dose-set position. Rather, the drive member 5 and the indicator element 3 still overlap in a side view of the assembly (see FIG. 6B).

However, in the present embodiment, the drive member 5 has a catch, which may for example be designed as a pocket 50 in the outer surface of the drive member. In one embodiment, the pocket has a distal opening and is bound in the proximal direction by at least one side wall.

When the indicator element 3 is in the first position and the drive member 5 is in the rest position, the deflectable end 3A of the strip 3 bears on a portion of the outer surface of the drive member which is at a distance from the catch 50 so that the strip 3 is disengaged from the catch 50. By moving the drive sleeve 5 from the rest position to the dose-set position, the strip 3 may be brought into engagement with the catch 50.

In particular, the deflectable end 3A bears on the outer surface of the drive sleeve 5 at a position which is proximal of the pocket 5 when the strip 3 is in the first position and the drive sleeve 5 is in the rest position. When the drive sleeve 5 is displaced in the first axial direction, e.g. proximally displaced, during operation of the assembly for the first time, the pocket 5 moves towards the deflectable end 3A until the deflectable end 3A of the strip 3 and the pocket 5 overlap so that the strip 3 engages the catch (pocket 50).

The deflectable end 3A can move radially inwardly from the deflected position to an undeflected position or at least to a less deflected position when the deflectable end 3A of the strip 3 overlaps with the pocket 50. In particular, the spring force induced by the resilient bias moves the deflectable end 3A from the resiliently biased position radially inwardly towards an interaction position once the drive sleeve 5 has reached the dose-set position during the first operation of the drive assembly. This situation is schematically illustrated in FIG. 6B.

In the interaction position, the drive sleeve 5 is operable to transfer the force for displacing the strip 3 away from the first angular position. In the resiliently biased position, drive sleeve 5 is in particular inoperable to move, in particular to rotate the strip 3.

In the present embodiment, the strip 3, in particular at least the nose or fin of the deflectable end 3A of the strip 3, is arranged in the pocket 5 of the drive sleeve 5 when the strip 3 is in the interaction position. Thus, for example, the proximal side wall or side walls of the pocket can interact with the strip 3, in particular with the nose or fin to transfer the force to the strip 3 for rotating the strip away from the first angular position.

The catch 50, in particular the proximal side wall or side walls of the pocket 50, are expediently designed such that the catch 50 is operable to convert axial movement of the drive sleeve 50 along the longitudinal axis AL into rotational movement of the indicator element 3 around the rotational axis AR. For example the proximal side wall or at least one proximal side wall of the pocket 50 is oblique with respect to the longitudinal axis AL, in particular it is neither parallel nor perpendicular to the longitudinal axis AL.

When the drive sleeve 5 is moved in the second axial direction from the dose-set position back to the rest position, it rotates the strip 3 around the rotational axis AR and displaces it away from the first angular position to a predetermined second position, which is a predetermined second angular position in the present embodiment (see FIG. 6C).

In the second angular position, the strip 3 is no longer visible through the window 4 from the outside of the housing body 1. In other words, it does not overlap with the window 4 in top view onto the window 4. Rather, drive sleeve 5 is visible through the window and laterally overlaps with the window 4 in top view of window 4 when it is in the rest position. The drive sleeve 5 and the indicator element, in particular the strip 3 and/or the symbol 30, may be coded with different colors.

Similarly to the third embodiment, strip 3 remains in the predetermined second angular position when the drive sleeve 5 is moved in the first and second axial directions for operating the drive assembly for a second time, whereas the piston rod 2 is displaced in the second axial direction by the drive sleeve 5.

When the drive sleeve 5 is in the dose-set position during operation of the drive assembly for the second time, the piston rod 2 may be visible through the window 4, in a similar fashion as illustrated and described in connection with the third embodiment in FIG. 5D. The piston rod 2 and the indicator element (strip 3 and/or symbol 30) may be coded with different colors.

Any invention incorporated in the present disclosure is not restricted to the exemplary embodiments by the description on the basis of that exemplary embodiments. Rather, the invention encompasses any new feature and also any combination of features, which in particular comprises any combination of features in the patent claims and any combination of features in the exemplary embodiments, even if this combination is not explicitly specified in the patent claims or exemplary embodiments.

The invention claimed is:

1. An assembly for a drug delivery device comprising a housing body having a longitudinal axis;
a drive assembly having a drive member, the drive member being configured to be axially displaced with respect to the housing body during operation of the drive assembly for at least one of (i) setting a dose of a drug or (ii) dispensing the dose of the drug; and
a display assembly having a display and an indicator element, the indicator element being axially displaceable with respect to the housing body along the longitudinal axis;
wherein
the display is configured such that it displays a first state through a window where the indicator element is only visible through the window when the indicator element is in a first position, and where the display switches to a second state when the indicator element is displaced away from the first position and is no longer visible through the window and only the drive member or another element of the drive assembly is visible through the window, and
the drive assembly is configured such that the drive member transfers a force to the indicator element which force displaces the indicator element away from the first position when the drive assembly carries out a priming step, where a switch from the first state to the second state occurs during the priming step when a first portion of the drug is dispensed for a first time,
wherein the drive member is operable to hold the indicator element in a resiliently biased position when the drive member is in a rest position;
wherein the drive member is inoperable to transfer said force to the indicator element when the indicator element is in the resiliently biased first position, and wherein the drive member is operable to transfer said force to the indicator element when the indicator element is in an interaction position; and
wherein the assembly is configured such that the indicator element can move radially from the resiliently biased position to the interaction position when the drive member is displaced by a predetermined distance from the rest position in a first axial direction.

2. The assembly of claim 1, wherein the display comprises a window in the housing body and the indicator element is visible through the window to display the first state.

3. The assembly of claim 2, wherein the drive member comprises a piston rod, the indicator element is fixed to the piston rod or formed integrally with the piston rod, and, when the display displays the second state, a portion of the piston rod which portion is free of the indicator element is visible through the window to display the second state.

4. The assembly of claim 1, wherein the drive member comprises a piston rod and the indicator element is fixed to the piston rod or formed integrally with the piston rod.

5. The assembly of claim 1, wherein the drive assembly is configured such that the indicator element is displaced from the first position to a predetermined second position when the drive assembly is operated for said first time.

6. The assembly of claim 5, wherein the indicator element remains in the second position when the drive assembly is subsequently operated after the first dispense of the drug.

7. The assembly of claim 5, wherein the drive member and the indicator element are decoupled from each other when the indicator element is in the second position.

8. The assembly of claim 1, wherein the drive assembly comprises a piston rod, the piston rod being axially displaceable with respect to the drive member and the housing body and the drive member is operable to transfer a force to the piston rod for axially displacing the piston rod when the drive member is displaced in the first and/or second axial direction.

9. The assembly of claim 1, wherein the indicator element and the drive member are operable to be axially displaced with respect to each other when the drive member is displaced in the first axial direction.

10. The assembly of claim 1, wherein the drive member is operable to transfer said force to the indicator element when the drive member is displaced in the second axial direction during operation of the drive assembly for said first time.

11. The assembly of claim 1, wherein the drive member is operable to hold the indicator element n a resiliently biased position before the drive assembly is operated for said first time.

12. A drug delivery device comprising an assembly according to claim 1, wherein the drug delivery device is configured to dispense at least one fixed dose of the drug.

13. The assembly of claim 1, where the drive member is configured to move relative to and independent of the indicator element when the indicator element is in the second state to dispense a second portion of the drug.

14. An assembly for a drug delivery device comprising
a housing body having a longitudinal axis;
a drive assembly having a drive member, the drive member being configured to be axially displaced with respect to the housing body during operation of the drive assembly for at least one of (i) setting a dose of a drug from a cartridge or (ii) dispensing the dose of the drug from the cartridge; and
a display assembly having a display and an indicator element, the indicator element being rotationally displaceable with respect to the housing body around a rotational axis which is inclined to the longitudinal axis;
wherein
the display is configured such that it displays a first state through a window where the indicator element is visible through the window when the indicator element is in a first position, and wherein the display switches to a second state when the indicator element is displaced away from the first position and is no longer visible through the window, and
the drive assembly is configured such that the drive member transfers a force to the indicator element which force displaces the indicator element away from the first position when the drive assembly carries out a priming step, where a switch from the first state to the second state occurs during the priming step when a first portion of the drug is dispensed for a first time,
where the indicator element remains displaced away from the first position when the drive assembly is subsequently operated, and
wherein the drive member is configured to be displaced in a first axial direction and subsequently in a second axial direction when the drive assembly is operated;
wherein the drive member is operable to hold the indicator element in a resiliently biased position when the drive member is in a rest position;
wherein the drive member is inoperable to transfer said force to the indicator element when the indicator element is in the resiliently biased position; and
wherein the drive member is operable to transfer said force to the indicator element when the indicator element is in an interaction position,
wherein the display assembly is configured such that the indicator element can move rotationally from the resiliently biased position to the interaction position when the drive member is displaced by a predetermined distance from the rest position in the first axial direction.

* * * * *